United States Patent [19]
King

[11] Patent Number: 5,114,951
[45] Date of Patent: May 19, 1992

[54] AGENTS FOR COMBATING MULTIPLE DRUG RESISTANCE

[75] Inventor: Ann C. King, Chapel Hill, N.C.

[73] Assignee: Burroughs Wellcome Company, Research Triangle Park, N.C.

[21] Appl. No.: 336,192

[22] Filed: Apr. 11, 1989

[51] Int. Cl.⁵ ............... A01N 43/42; A61K 31/44; A61K 31/445
[52] U.S. Cl. ............................ 514/290; 514/325; 424/10
[58] Field of Search ............... 424/10; 514/290, 325

[56] References Cited

U.S. PATENT DOCUMENTS 4,628,047 12/1986 Sakurai et al. ............ 514/34
4,990,538 2/1991 Harris et al. ............... 514/648

FOREIGN PATENT DOCUMENTS 0270926 6/1988 European Pat. Off. .
61-85320 4/1986 Japan .

OTHER PUBLICATIONS

Inaba et al., *Cancer Research,* Reversal of Resistance to Vencristine in P388 Leukemia by Various Polycyclic Clinical Drugs, with a Special Emphasis on Quinacrine, 48, 2064–2067, Apr. 15, 1988.
Wilson, C. M. et al., "Amplification of a Gene Related to Mammalian mdr Genes in Drug-Resistant Plasmodium Falciparum," *Science* 244, 1184 (1989).
"The Merck Index," p. Misc-2 (11th Ed. 1989).
Fine, R. L. and Chabner, B. A., *Cancer Chemotherapy* 8, 117 (1986).
Fojo, A. T. et al., *Journal of Clinical Oncology* 5, No. 12, 1922 (1987).
Fojo, A. et al., *Cancer Research* 45, 3002 (1985).
Goldstein, L. J. et al., *Journal of the National Cancer Institute* 81, No. 2, 116 (1989).
Gottesman, M. M. and Pastan, I., *The Journal of Biological Chemistry* 263, No. 25, 12163 (1988).
Housman, D. et al., "A Molecular Genetic Approach to the Problem of Drug Resistance in Chemotherapy" in *New Avenues in Developmental Cancer Chemotherapy,* 503 (Academic Press, Inc., 1987).
Pastan, I. and Gottesman, M., *The New England Journal of Medicine* 316, No. 22, 1388 (1987).

*Primary Examiner*—Nathan M. Nutter
*Attorney, Agent, or Firm*—Bell, Seltzer, Park & Gibson

[57] ABSTRACT

Potentiating agents for combatting multiple drug resistance of susceptible tumor cells in a subject in need of such treatment are disclosed. The potentiating agents disclosed are triprolidine, cis-triprolidine, and pharmaceutically acceptable salts thereof.

2 Claims, No Drawings

AGENTS FOR COMBATING MULTIPLE DRUG RESISTANCE

FIELD OF THE INVENTION

The present invention relates to the use of triprolidine and triprolidine-like compounds as adjuvant chemotherapy for neoplasias resistant to multiple drugs. The present invention also relates to the use of triprolidine-like compounds as an agent for enhancing the therapeutic effect of multiple antitumor agents.

BACKGROUND OF THE INVENTION

Complete cures of various tumors like leukemias, lymphomas and solid tumors by the use of chemotherapeutic agents are rare because of heterogeneous sensitivity of tumor cells to each antitumor agent. Cancer chemotherapy also fails because of intrinsic resistance of tumors to multiple drug therapies. In other cases, a tumor may become resistant to the antitumor agents used in a previous treatment. The therapeutic effects of these agents are then eliminated. An even graver problem is that recurrent cancers are resistant not only to the cancer suppressants used in previous treatments, but also manifest resistance to other antitumor agents, unrelated to the agent used previously either by chemical structure or by mechanism of action. These phenomenon are collectively referred to as multiple drug resistance (mdr) and contribute widely to cancer treatment failures in the clinic.

The major documented cause of multiple drug resistance is overexpression of a membrane glycoprotein (the multiple drug transporter) responsible for pumping structurally diverse antitumor drugs from cells. See D. Houseman et al., *A Molecular Genetic Approach to the Problem of Drug Resistance in Chemotherapy*, 504-517 (1987) (Academic Press, Inc.); R. Fine and B. Chabner, *Multidrug Resistance, in Cancer Chemotherapy* 8, 117-128 (H. Pinedo and B. Chabner eds. 1986).

Tumor cells expressing elevated levels of the multiple drug transporter accumulate far less antitumor agents intracellularly than tumor cells having low levels of this enzyme. The degree of resistance of certain tumor cells has been documented to correlate with both elevated expression of the drug transporter and reduced accumulation of antitumor drugs. See M. Gottesman and I. Pastan, *J. Biol. Chem.* 263, 12163 (1988); see also A. Fojo et al., *Cancer Res.* 45, 3002 (1985). This form of multiple drug cross-resistance involves agents derived from natural products, such as the vinca alkaloids, the anthracyclines, the epipodophyllotoxins, actinomycin D and plicamycin. See I. Pastan and M. Gottesman, *New England J. Med.* 1388, 1389 Table 1 (May 28, 1987).

Adenocarcinomas derived from adrenal, kidney, liver, small intestine, and colon tissue are notorious for exhibiting inherent cross-resistance to chemically unrelated chemotherapeutic agents. See M. Gottesman and I. Pastan, supra at 12165; see also A. Fojo et al., *J. Clin. Oncol.* 5, 1922 (1987). These tissues normally express higher levels of the multidrug transporter. Other tumors documented to express high levels of the multidrug transporter include pancreatic, carcinoid, chronic myelogenous leukemia in blast crisis, and non-small cell lung carcinoma. Tumors documented to initially be drug-sensitive but to then become drug resistant include neuroblastoma, pheochromocytoma, acute lymphocytic leukemia in adults, acute nonlymphocytic leukemia in adults, nodular poorly differentiated lymphoma, breast cancer and ovarian cancers. It is estimated by the National Cancer Institute that approximately half a million tumor samples a year will be drug resistant because of aberrant levels of expression of the multidrug transporter. See L. Goldstein et al., Expression of Multidrug Resistance Gene in Human Cancers, *J. National Cancer Institute* 81, 116 (1988).

Elevated levels of expression of the mdr drug transporter in these tumors would lead to reduced intracellular levels of antitumor agents in the tumor and would cause suppression of chemotherapeutic efficacy. Tumors having elevated levels of the multiple drug transporter would require therapeutic doses of cancer suppressants far in excess of tumors exhibiting lower levels of the mdr drug transporter. Agents that inhibit the active efflux of antitumor agents by the drug transporter or agents that potentiate the efficacy of chemotherapeutic agents would enhance the activity of various antitumor agents on tumor cells. As a result of the present inventor's study, it has unexpectedly been found that when the agents disclosed herein are used together with an antitumor agent, they enhance the therapeutic effect of the antitumor agent.

A number of agents used clinically as calcium channel-blockers, calmodulin inhibitors and antiarrhythmic agents promote the activity of antitumor agents against resistant tumor cells, see Tsuruo et al., *Cancer Res.* 44, 4303 (1984); 43, 2267 (1983). Verapamil, caroverine, clomipramine, trifluoperazine, prenylamine, diltiazem, nicardipine, and quinidine enhance the activity of antitumor agents against resistant sublines of murine leukemia cells. Most agents potentiating the activity of antitumor agents are calcium antagonists, and the serious cardiotoxicities that arise during treatment have limited their clinical usefulness. While the inventor does not wish to be bound by any theory of operation for the present invention, it is noted that the agents disclosed herein are not known to have calcium antagonism. They have, however, been found to elevate the intracellular concentration of antineoplastic drugs in tumor cells overexpressing the multiple drug transporter. Sensitization of drug resistant tumors and elevation of intracellular antitumor drug concentrations probably occur by a mechanism different from calcium antagonism.

SUMMARY OF THE INVENTION

An object of the present invention is to provide an agent for enhancing the therapeutic effect of an antineoplastic agent by administering to a subject harboring a tumor a compound of Formula (I) below (triprolidine), a compound of Formula (II) below (cis-triprolidine), or a pharmaceutically acceptable salt thereof (hereafter referred to as the "potentiating agent").

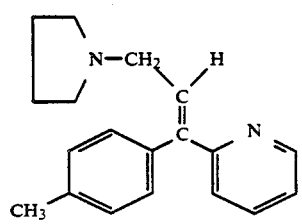

I

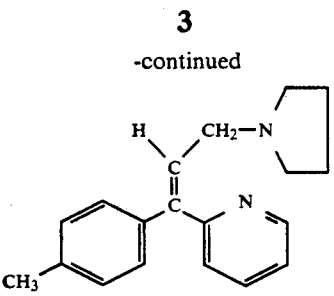

II

Another aspect of the present invention is a method of inhibiting multiple drug resistance in a subject in need of such treatment by administering the subject a potentiating agent in an amount effective to combat multiple drug resistance.

DETAILED DESCRIPTION OF THE INVENTION

Potentiating agents exemplary of the present invention include:

(A) Triprolidine; and
(B) Z-2-[3-(1-Pyrrolidinyl) -1- (4-tolyl)-1-propenyl]-pyridine hydrochloride, or cis-Triprolidine. These compounds are known. See, e.g., R. Ison et al., *J. Pharm. Pharmac.* 25, 887 (1973).

A preferred category of multiple drug resistant tumor cells to be treated by the method of the present invention are multiple drug resistant cells characterized by the multidrug transporter—mediated pumping of antineoplastic agents out of the tumor cells. The multidrug transporter protein is described in M. Gottesman and I. Pastan, supra. Thus, tumor cells treated by the present invention are preferably those characterized by (a) the expression of the multidrug transporter protein at high levels, or (b) the ability to express the multidrug transporter protein upon selection by an antineoplastic agent.

Exemplary of tumor cells which express the multidrug transporter at high levels (intrinsically resistant cells) are adenocarcinoma cells, pancreatic tumor cells, carcinoid tumor cells, chronic myelogenous leukemia cells in blast crisis, and non-small cell lung carcinoma cells.

Exemplary of tumor cells having the ability to express the multidrug transporter protein upon selection by an antineoplastic agent are neuroblastoma cells, pheochromocytoma cells, adult acute lymphocytic leukemia cells, adult acute nonlymphocytic leukemia cells, nodular poorly differentiated lymphoma cells, breast cancer cells and ovarian cancer cells.

A preferred group of tumor cells for treatment in the present invention are the adenocarcinomas, including adenocarcinomas of adrenal, kidney, liver, small intestine and colon tissue, with kidney adenocarcinoma cells particularly preferred.

Preferred antineoplastic agents for use in the present invention are those to which multidrug transporter—mediated multiple drug resistant cells develop resistance. Exemplary of such antineoplastic agents are vinca alkaloids, epipodophyllotoxins, anthracycline antibiotics, actinomycin D, plicamycin, puromycin, gramicidin D, taxol, colchicine, cytochalasin B, emetine, maytansine, and amsacrine (or "mAMSA"). Preferred are vinca alkaloids, epipodophyllotoxins, anthracyclene antibiotics, actinomycin D, and plicamyoin.

The vinca alkaloid class is described in *Goodman and Gilman's The Pharmacological Basis of Therapeutics,* 1277-1280 (7th ed. 1985) (hereafter "Goodman and Gilman"). Exemplary of vinca alkaloids are vincristine, vinblastine, and vindesine.

The epipodophyllotoxin class is described in Goodman and Gilman, supra at 1280-1281. Exemplary of epipodophyllotoxins are etoposide, etoposide orthoquinone, and teniposide.

The anthracycline antibiotic class is described in Goodman and Gilman, supra at 1283-1285. Exemplary of anthracycline antibiotics are daunorubicin, doxorubicin, mitoxantraone, and bisanthrene. Daunorubicin and doxorubicin are preferred.

Actinomycin D, also called Dactinomycin, is described in Goodman and Gilman, supra at 1281-1283. Plicamycin, also called mithramycin, is described in Goodman and Gilman, supra at 1287-1288.

Subjects to be treated by the method of the present invention include both human and animal (e.g., dog, cat, cow, horse) subjects, and are preferably mammalian subjects.

The potentiating agent is administered in an amount effective to enhance the efficacy of the antineoplastic agent. The potentiating agent is preferably administered in a total amount per day of not more than about 50 mg/kg body weight, more preferably not more than about 25 mg/kg, and most preferably not more than about 5 mg/kg. With respect to minimum dose, the potentiating agent is preferably administered in a total amount per day of at least about 0.01 mg/kg, more preferably at least about 0.1 mg/kg, and most preferably at least about 1 mg/kg. The potentiating agent may be administered once or several times a day.

As noted above, compounds of Formulas (I) and (II) may be administered per se or in the form of a pharmaceutically acceptable salt. When used in medicine, the salts of the compound of Formulas (I) and (II) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulphuric, nitric, phosphoric, maleic, salicylic, p-toluenesulfonic, tartaric, citric, methanesulphonic, formic, malonic, succinic, naphthalene-2-sulphonic and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical formulations, both for veterinary and for human medical use, which comprise the potentiating agent together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof.

Pharmaceutical formulations of the present invention may optionally include an antineoplastic agent, preferably an agent as described above. Such a formulation is useful for concurrently administering an antineoplastic agent and the potentiating agent in a method as described above.

The formulations include those suitable for oral, rectal, topical, nasal, ophthalmic or parenteral (including subcutaneous, intramuscular and intravenous) administration. Formulations suitable for oral and parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations of the present invention suitable for oral administration may be presented as discrete units such as capsules, cachets, tablets or lozenges, each containing a predetermined amount of the potentiating agent as a powder or granules; or a suspension in an aqueous liquor or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with a suitable carrier may be made by molding in a suitable machine.

A syrup may be made by adding the active compound to a concentrated aqueous solution of a sugar, for example sucrose to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

Formulations suitable for parenteral administration conveniently comprise a sterile aqueous preparation of the active compound, which is preferably isotonic with the blood of the recipient.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

The following Examples are provided to illustrate the present invention, and should not be construed as limiting thereof. Temperatures are given in degrees Celsius unless otherwise indicated.

EXAMPLE 1

In Vitro Cytotoxicity of Potentiating Agents in Chinese Hamster Ovary Cells

Chinese hamster ovary (CHO) tissue culture cells were obtained from Dr. Vic Ling, Princess Margaret Hospital, Toronto, Canada. The parental cell line (AuxB1) and a multidrug resistant line (C5S32) having an amplified form of the MDR drug transport protein were plated into 96-well microtitre culture dishes at 250 or 500 cells per well in minimal essential medium, type alpha, 10% fetal calf serum and incubated in 95% oxygen/5% carbon dioxide for 48 hours. After this period, the medium was changed and one-half of the culture was treated with Actinomycin D (Act D) (0.01 $\mu$M for AuxB1 cells and 0.5 $\mu$M for C5S32 cells). C5S32 cells are about 200-fold resistant to Actinomycin D compared to the parental AuxB1 cell line. In addition to Act D some of the cultures also received a dose of the potentiating agent at 1 and 10 $\mu$M. Thus, four conditions were tested in each screening assay: untreated cells in medium alone, cells receiving Act D alone, cells incubated with the potentiating agent alone, and cells incubated with a combination of Act D and the potentiating agent. Both the parental and mdr cell lines were treated with these four conditions simultaneously. Each experimental condition reported below is based on the average absorbance from eight replicate samples. The incubation with Act D and the test drug continued for 96 additional hours, after which 0.5 mg/ml MTT dye was added to the cultures and allowed to incubate for three hours. The cells were solubilized by addition of DMSO and the absorbance at 570 nm was monitored. The absorbance is directly related to the number of surviving cells in the culture dish.

In Table 1 below, the absorbance was normalized so that cytotoxicity of the potentiating agent could be evaluated. Untreated cultures were given a value of 1.00 and the cultures receiving 1 and 10 $\mu$M of the potentiating agent are reported as a fraction of this value. To evaluate the compounds for inducing synergism with Actinomycin D, the absorbance values of cultures receiving Act D alone were assigned a value of 1.00 and cultures receiving the combination of Act D and potentiating agent Act D are reported as a fraction of this control. In most experiments, this concentration of Act D gave a reduction in cell number 10-20% below the value of completely untreated cultures.

TABLE 1

In Vitro Cytotoxicity of Potentiating Agents in Chinese Hamster Ovary Cells

| Compound | Dose | Wildtype AUXBI | | Drug Resistant C5S32 | |
|---|---|---|---|---|---|
| | | 0 | +ACT D | 0 | +ACT D |
| (A) | 1 $\mu$M | 1.00 | 1.00 | 0.83 | 0.80 |
| | 10 $\mu$M | 1.00 | 1.00 | 0.73 | 0.72 |
| (B) | 1 $\mu$M | 0.96 | 0.78 | 0.70 | 0.82 |
| | 10 $\mu$M | 0.91 | 0.60 | 0.22 | 0.35 |

EXAMPLE 2

In Vitro Cytotoxicity of Potentiating Agents in Human KB Epidermoid Carcinoma Cells The procedure for assaying the cytotoxicity of potentiating agents with human KB epidermoid carcinoma cells is essentially the same as the assay procedure described above for use with Chinese hamster ovary cells. In brief, KB 3-1 (wt) and KB V-1 (mdr) cells are plated at 500 cells/well in 96-well culture plates in Dulbecco's modified eagle medium, supplemented with 10% fetal calf serum. After 48 hours of incubation at 37° C., the media is changed and cells are treated with actinomycin D at 0.1 nM (3-1) or 20 nM (V-1). The test potentiating agent is introduced to one-half the untreated cultures and one-half the Act D treated cultures at 1 and 10 μM. After 96 hours of additional incubation at 37° C., 0.5 mg/ml MTT dye is added, the cells are incubated for three hours, after which the cells are dissolved in DMSO, and the absorbance is then read at 570 nm. The data is given in Table 2 below.

TABLE 2

In Vitro Cytotoxicity of Potentiating Agents in Human KB Epidermoid Carcinoma Cells

| Compound | Dose | Wildtype KB 3-1 | | Drug Resistant KB V-1 | |
| --- | --- | --- | --- | --- | --- |
| | | 0 | +ACT D | 0 | +ACT D |
| (A) | 1 μM | 1.00 | 1.00 | 0.83 | 0.94 |
| | 10 μM | 0.89 | 1.00 | 0.69 | 0.64 |
| (B) | 1 μM | 1.00 | 1.00 | 1.00 | 1.00 |
| | 10 μM | 0.87 | 1.00 | 0.72 | 0.88 |

The foregoing examples are illustrative of the present invention, and are not to be taken as restrictive thereof. The invention is defined by the following claims, with equivalents of the claims to be included therein.

That which is claimed is:

1. A method of combating multiple drug resistance of susceptible tumor cells in a subject in need of such treatment, comprising administering to the subject a compound, in an amount effective to combat multiple drug resistance of tumor cells sensitive to said compound, wherein said compound is selected from the group consisting of triprolidine, cis-triprolidine, and pharmaceutically acceptable salts thereof.

2. A method according to claim 1, wherein said tumor cells are adenocarcinoma cells.

* * * * *